(12) United States Patent
Matsui et al.

(10) Patent No.: US 10,969,377 B2
(45) Date of Patent: Apr. 6, 2021

(54) BIOPOLYMER ANALYSIS DEVICE AND BIOPOLYMER ANALYSIS METHOD

(71) Applicant: HITACHI, LTD., Tokyo (JP)

(72) Inventors: Kazuma Matsui, Tokyo (JP); Itaru Yanagi, Tokyo (JP); Kenichi Takeda, Tokyo (JP)

(73) Assignee: HITACHI, LTD., Tokyo (JP)

( * ) Notice: Subject to any disclaimer, the term of this patent is extended or adjusted under 35 U.S.C. 154(b) by 85 days.

(21) Appl. No.: 15/513,133

(22) PCT Filed: Nov. 12, 2014

(86) PCT No.: PCT/JP2014/079904
§ 371 (c)(1),
(2) Date: Mar. 21, 2017

(87) PCT Pub. No.: WO2016/075764
PCT Pub. Date: May 19, 2016

(65) Prior Publication Data
US 2017/0299572 A1 Oct. 19, 2017

(51) Int. Cl.
*G01N 33/487* (2006.01)
*G01N 27/447* (2006.01)
*C12Q 1/6869* (2018.01)

(52) U.S. Cl.
CPC ..... *G01N 33/48721* (2013.01); *C12Q 1/6869* (2013.01); *G01N 27/44791* (2013.01)

(58) Field of Classification Search
CPC ......... G01N 33/48721; G01N 27/3278; G01N 27/44791; C12Q 1/6869
See application file for complete search history.

(56) References Cited

U.S. PATENT DOCUMENTS

| 6,068,751 A * | 5/2000 | Neukermans ..... B01L 3/502715 137/606 |
| 2010/0066348 A1* | 3/2010 | Merz ..................... C12Q 1/6869 324/71.1 |

(Continued)

FOREIGN PATENT DOCUMENTS

| JP | 2012-026986 A | 2/2012 |
| JP | 2012026986 A * | 2/2012 |

(Continued)

OTHER PUBLICATIONS

International Search Report and Written Opinion for PCT App No. PCT/JP2014/079904 dated Feb. 17, 2015, 9 pgs.

(Continued)

*Primary Examiner* — James Lin
*Assistant Examiner* — Vivian A Tran
(74) *Attorney, Agent, or Firm* — Procopio, Cory, Hargreaves & Savitch LLP

(57) ABSTRACT

An apparatus for a thin film device is used for analyzing a biopolymer. The apparatus has a thin film, a first solution in contact with a first surface of the thin film, a second solution in contact with a second surface of the thin film, a flow path or a conductive wire for adjusting the potential difference between the first solution and the second solution to a small value, a control unit for controlling the flow path or the conductive wire, an inlet from which a biopolymer is introduced to at least one of the first and second solution, a first electrode provided in the first solution, a second electrode provided in the second solution and an ammeter for measuring the current which flows between the first and second electrode when the biopolymer passes through a hole in the thin film between the first and second solution.

9 Claims, 15 Drawing Sheets

(56) References Cited

U.S. PATENT DOCUMENTS

| | | | | |
|---|---|---|---|---|
| 2011/0308950 | A1* | 12/2011 | Sakai | G01N 33/6803 |
| | | | | 204/452 |
| 2012/0097539 | A1* | 4/2012 | Qian | B82Y 40/00 |
| | | | | 204/451 |
| 2013/0264219 | A1* | 10/2013 | Afzali-Ardakani | B82Y 15/00 |
| | | | | 205/703 |

FOREIGN PATENT DOCUMENTS

| | | | |
|---|---|---|---|
| JP | 2014-190891 A | 10/2014 | |
| WO | WO-2014024598 A1 * | 2/2014 | G01N 27/4145 |

OTHER PUBLICATIONS

Kumar, A., et al., Noise and its Reduction in Graphene Based Nanopore Devices, Nanotechnology 24, 495503, 2013, 7 pgs.

Venta, K., et al., Differentiation of Short, Single-Stranded DNA Homopolymers in Solid-State Nanopores, ACS Nano, 2013, 7(5), pp. 4629-4636.

* cited by examiner

[FIG. 1]
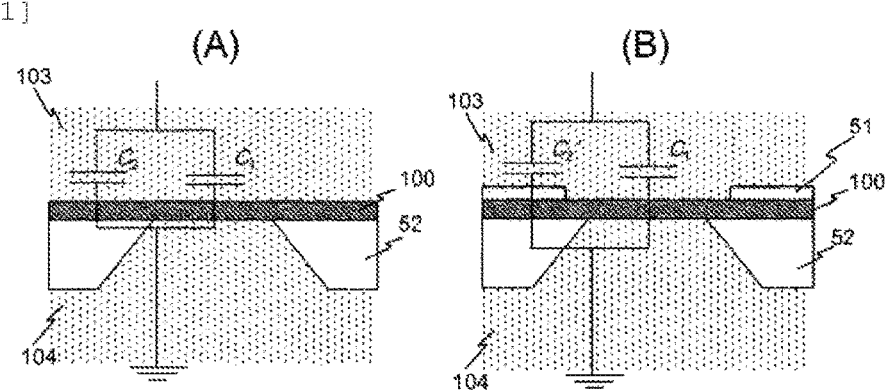
[FIG. 2]
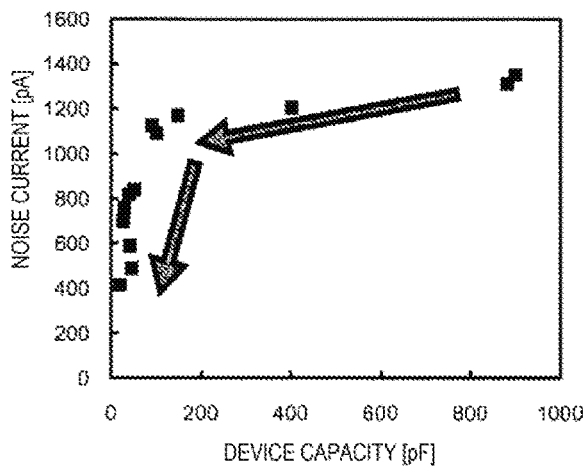
[FIG. 3]
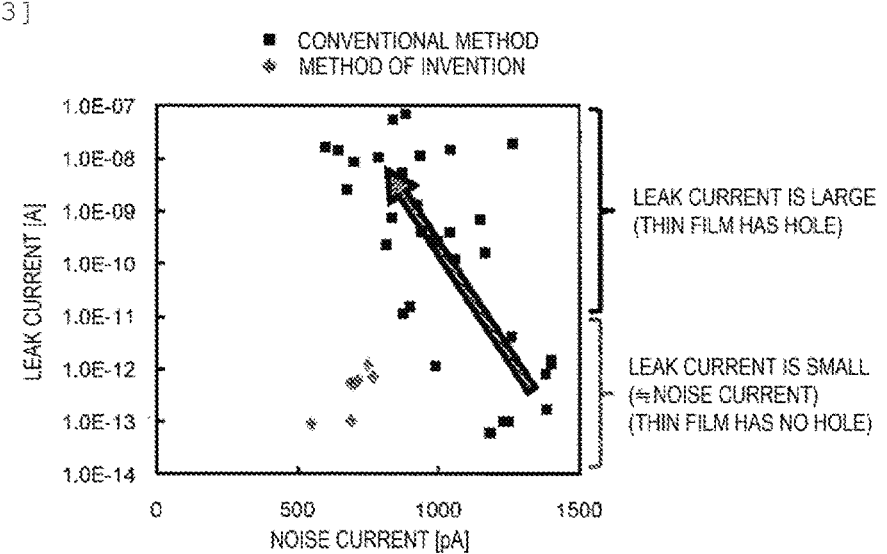

[FIG. 4]
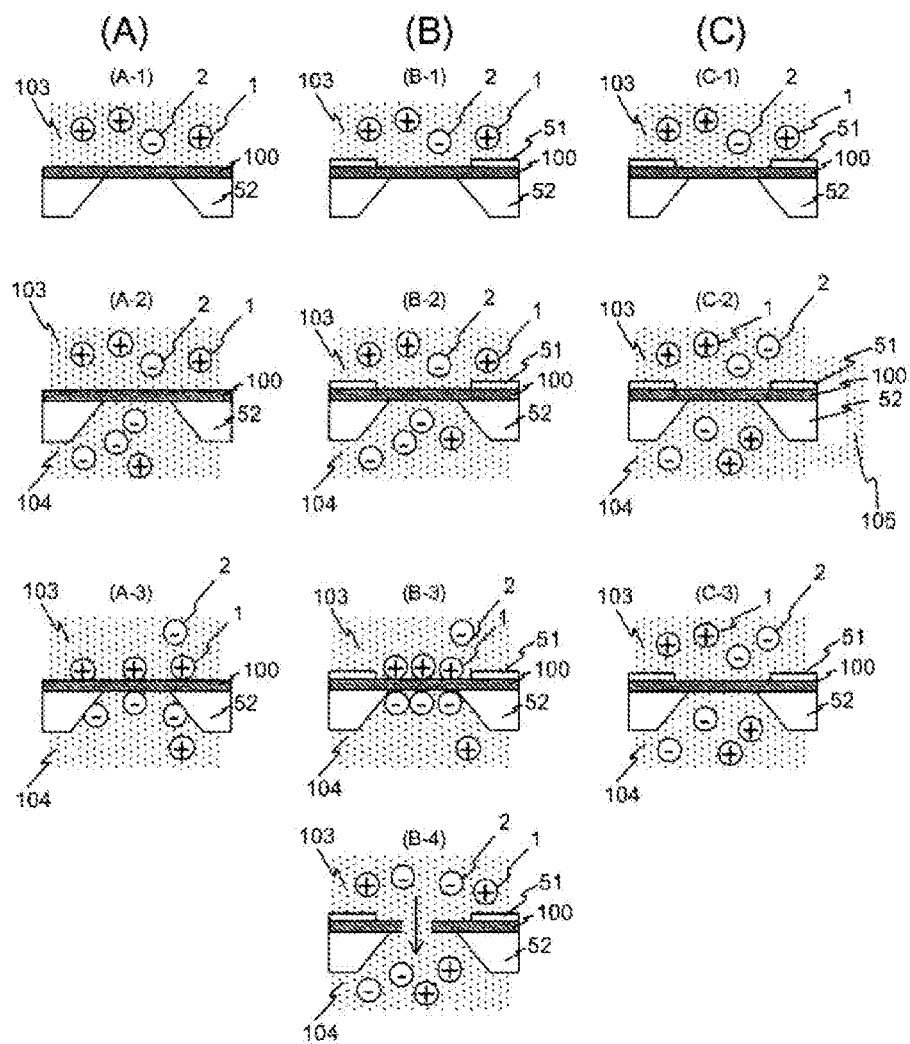

[FIG. 5]
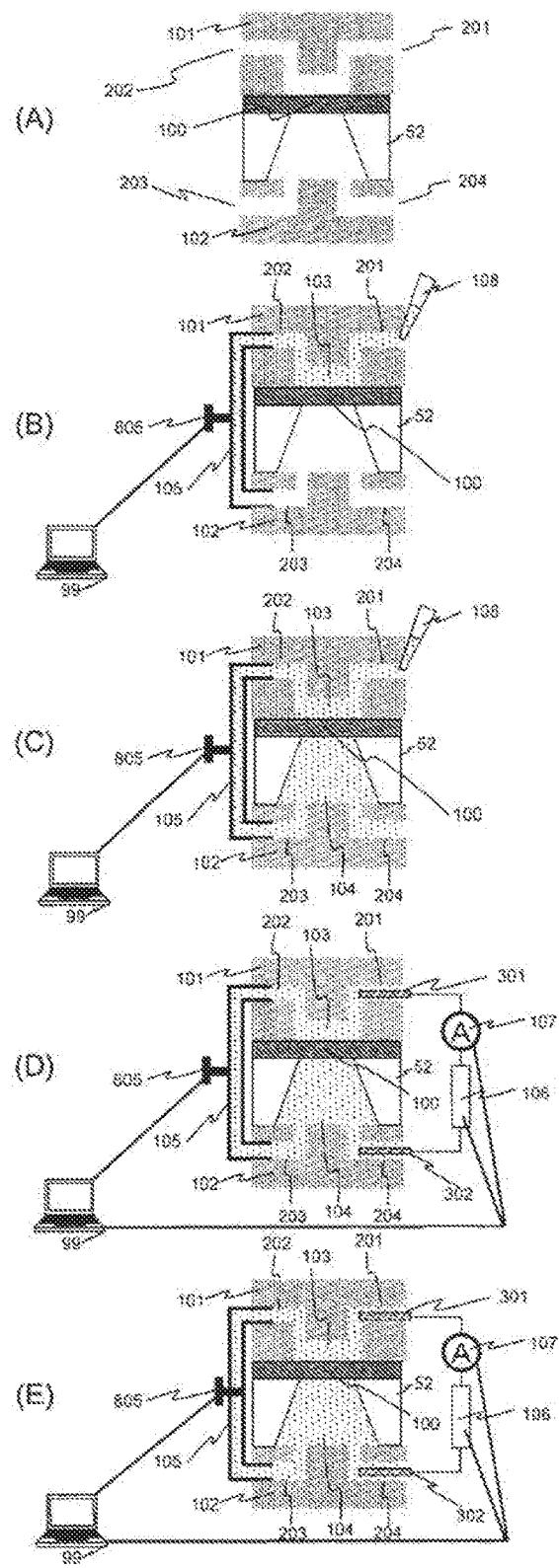

[FIG. 6]
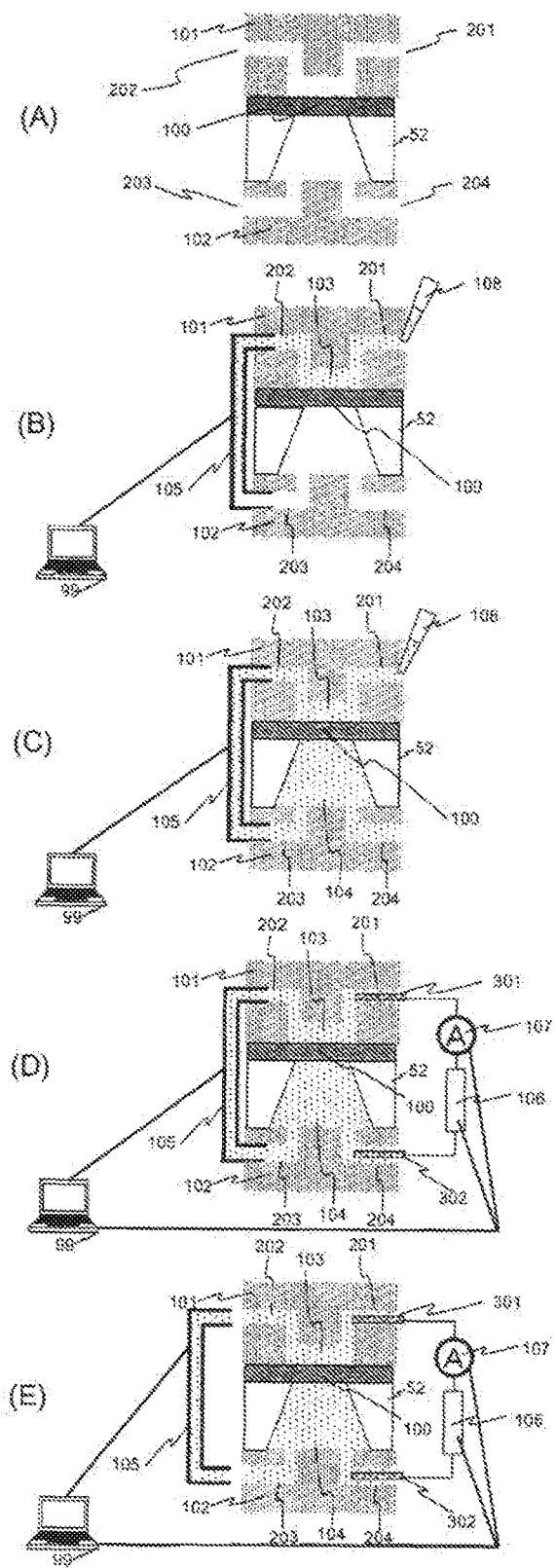

[FIG. 7]
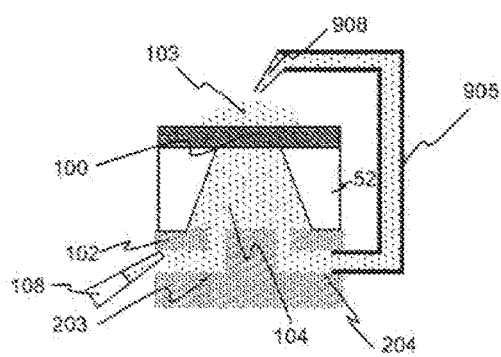
[FIG. 8]
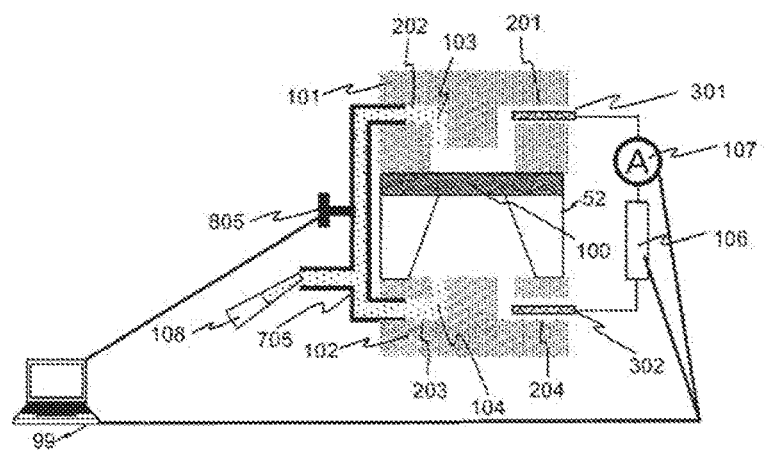
[FIG. 9]
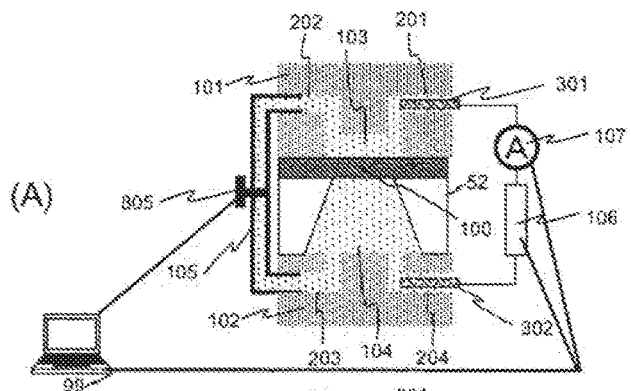
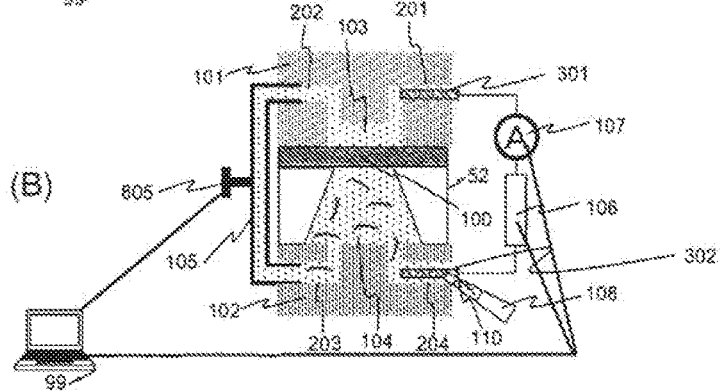

[FIG. 10]
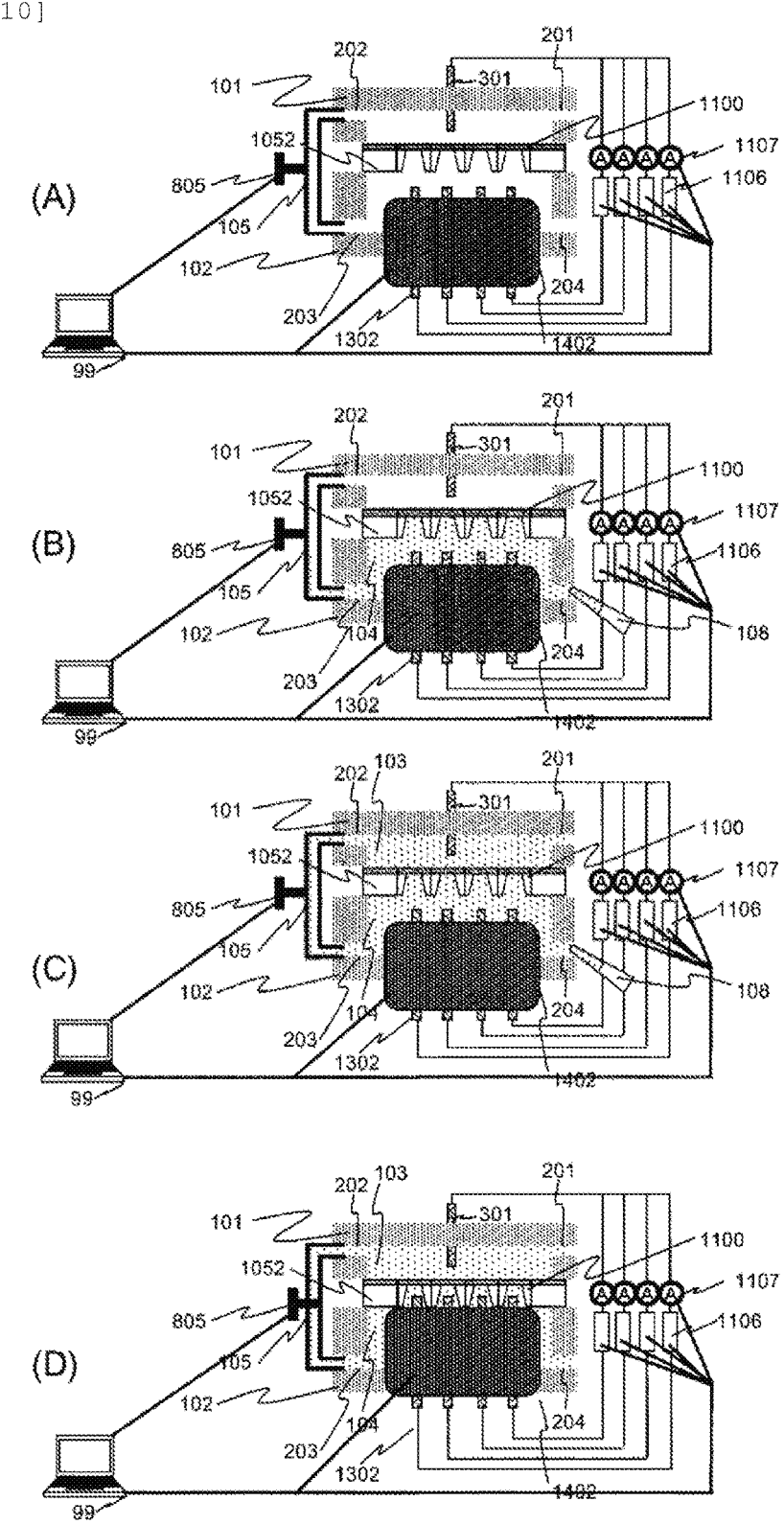

[FIG. 11]
(A)
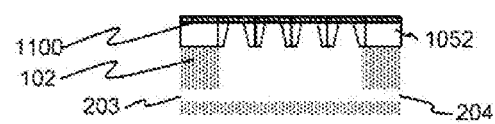
(B)
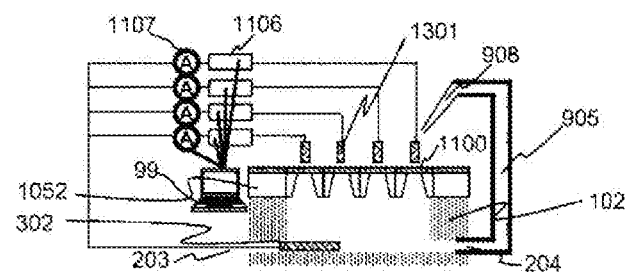
(C)
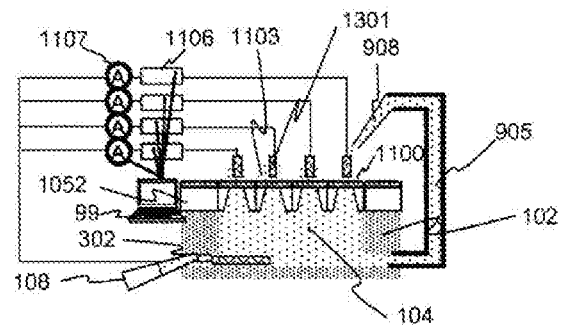

[FIG. 12]
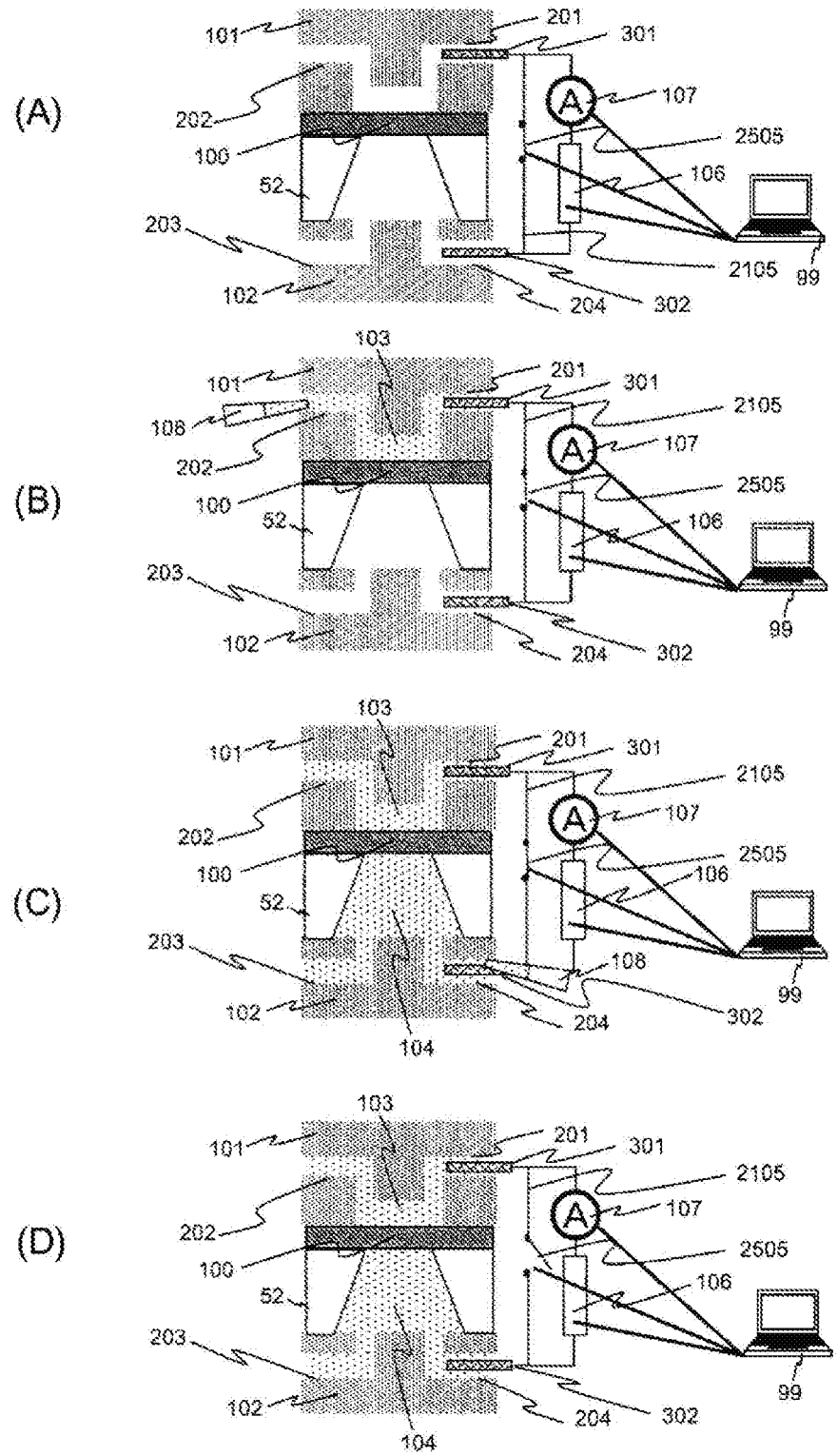

[FIG. 13]
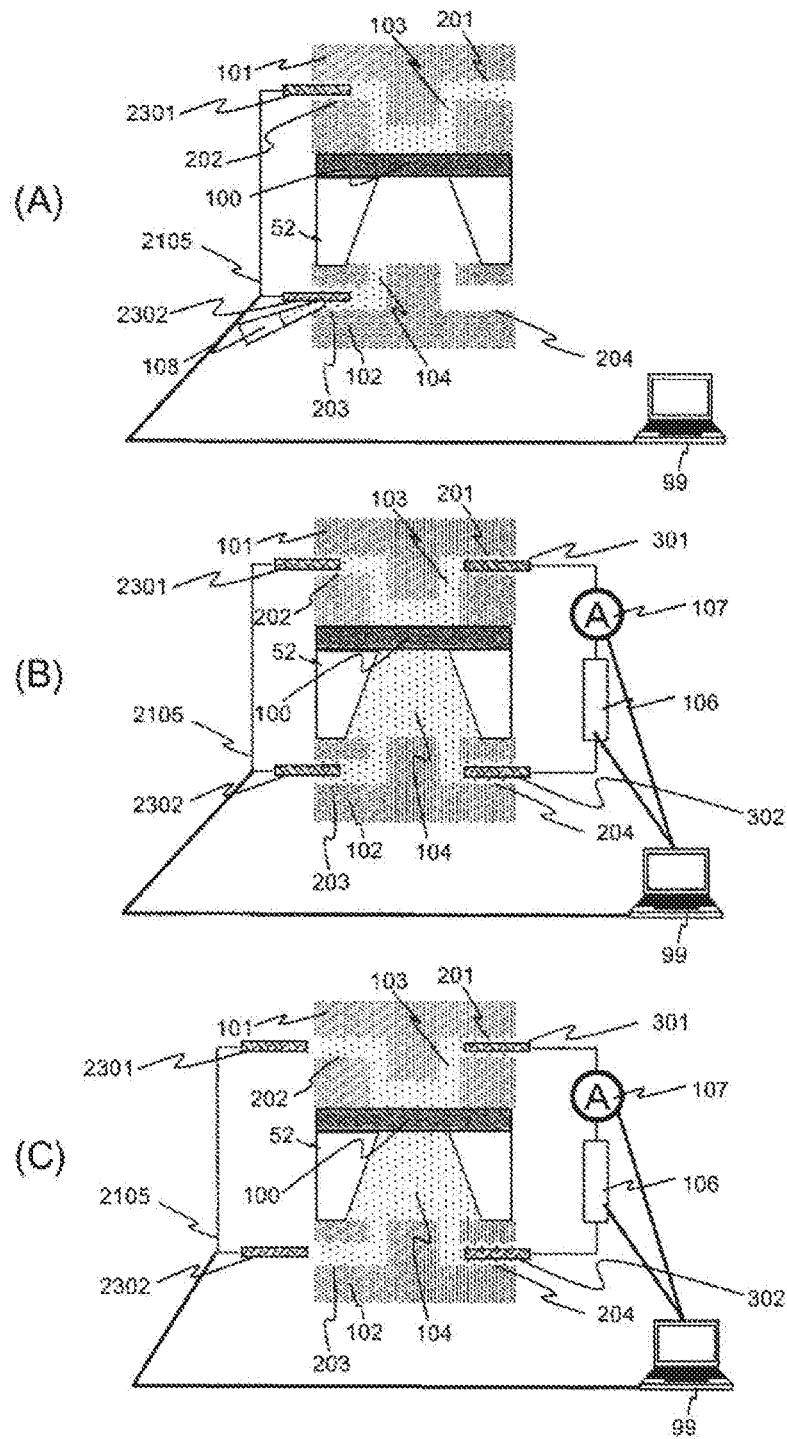

[FIG. 14]
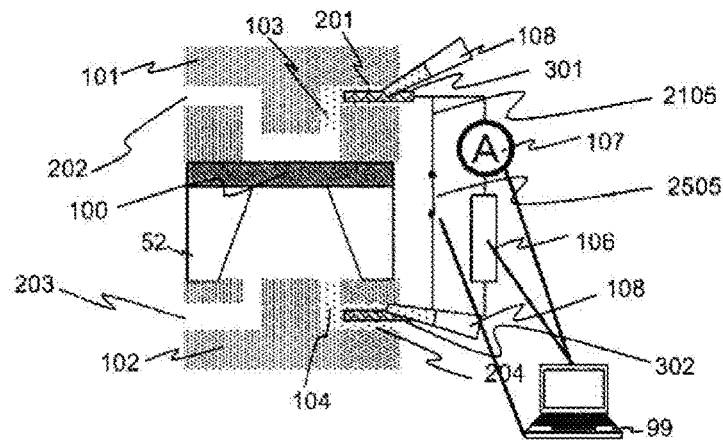
[FIG. 15]
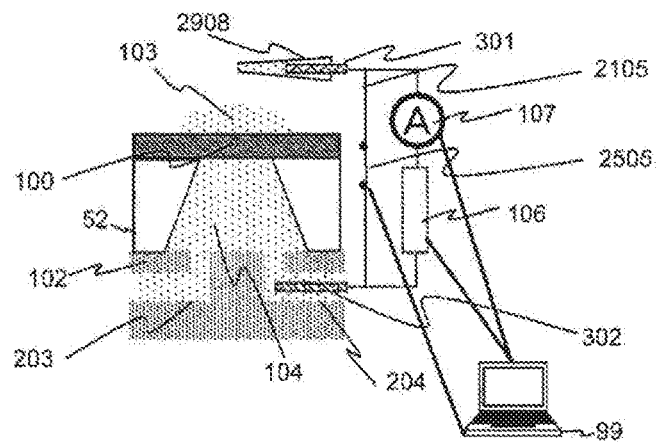

[FIG. 16]
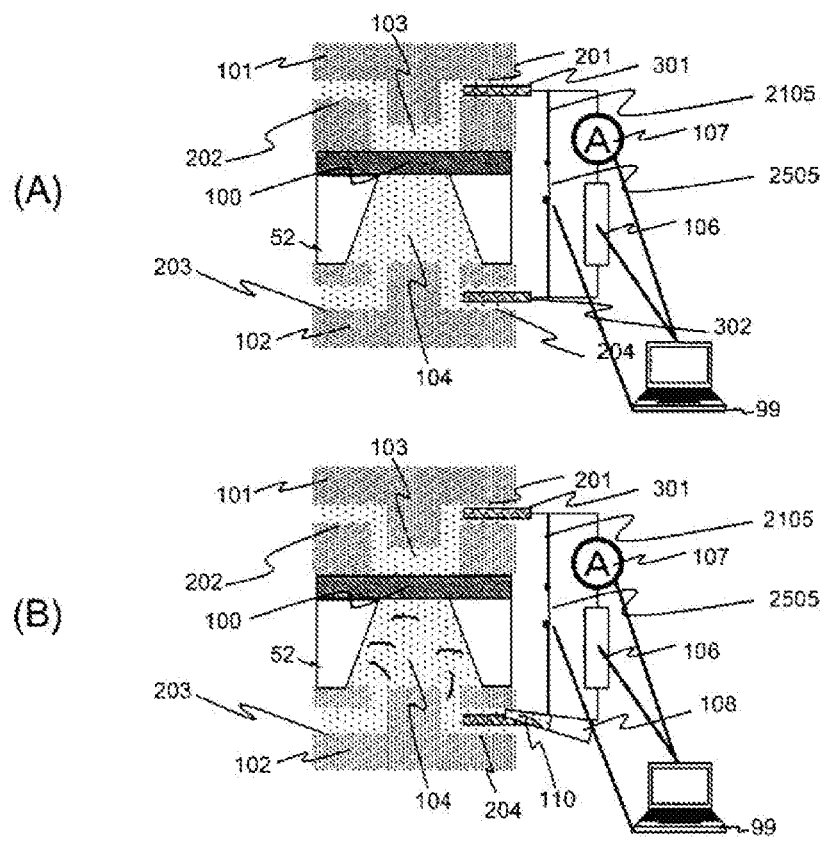

[FIG. 17]
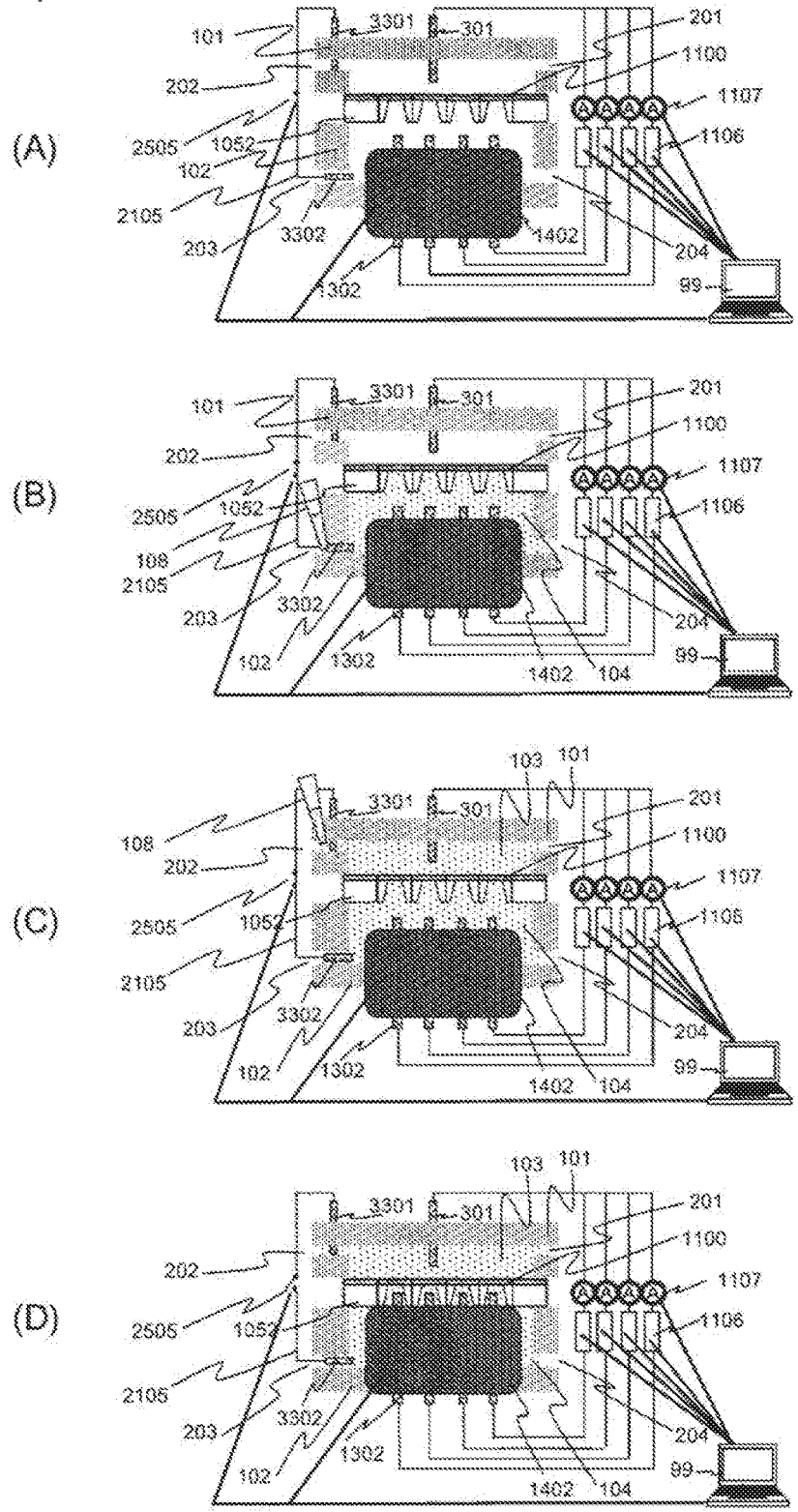

[FIG. 18]
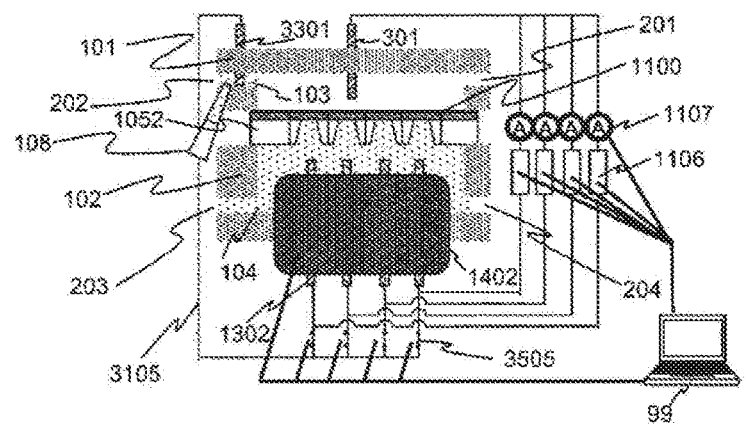
[FIG. 19]
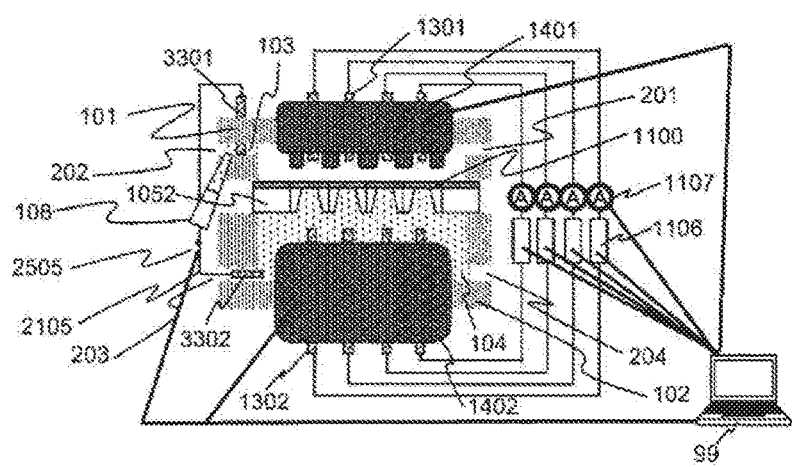
[FIG. 20]
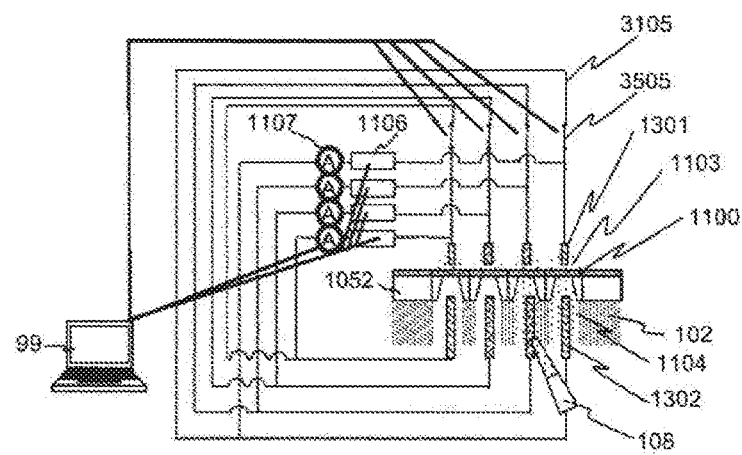

[FIG 21]
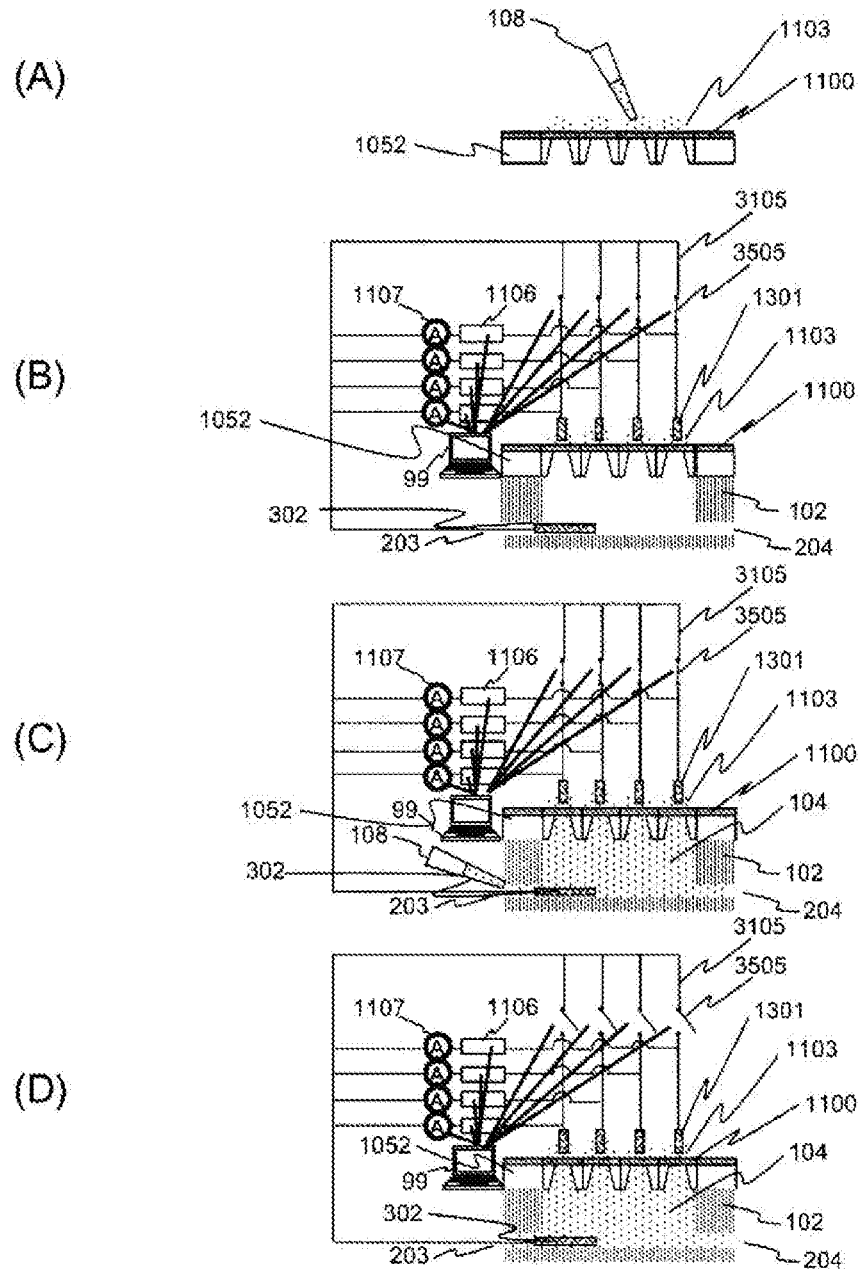

[FIG. 22]
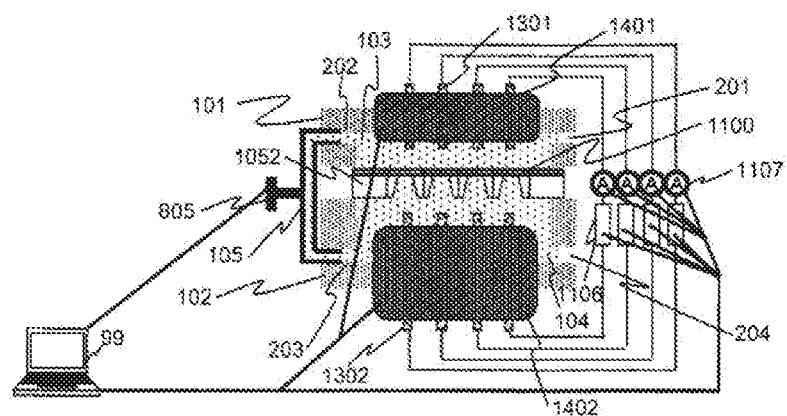

BIOPOLYMER ANALYSIS DEVICE AND BIOPOLYMER ANALYSIS METHOD

CROSS-REFERENCE TO RELATED APPLICATIONS

This application is a U.S. National Stage entry of PCT Application No. PCT/JP2014/079904, filed on Nov. 12, 2014, the contents of which are incorporated herein by reference.

TECHNICAL FIELD

The present invention belongs to a technical field related to a structure and a method for analyzing a biopolymer using a thin film device.

BACKGROUND ART

In a nanopore sequencer, the value of the current flowing through a nanopore embedded in a thin film is measured. At this point, when DNA passes through the nanopore, a difference in the value of the current blocking the nanopore (blockage current value) is caused due to the difference in the bases constituting the DNA, and the nucleotide sequence can be thus determined.

Factors that determine the accuracy in reading DNA with a nanopore sequencer include the thickness of the thin film, the level of the noise in the current flowing through the nanopore and the like. With respect to the thickness of the thin film, a thinner film is preferable. The distance between neighboring bases of the four kinds aligning in a DNA chain is approximately 0.34 nm, and more bases enter the nanopore at the same time as the film becomes thicker as compared to the distance. As a result, the signal obtained as the blockage current becomes the signal derived from more than one base. Thus, the accuracy in determining the nucleotide sequence deteriorates, and the analysis of the signal becomes more complex. Moreover, a smaller noise current is preferable. Because the value of the blockage current is a value to which the noise current value has been added, it is necessary to reduce the blockage current to increase the identification rate of the four kinds of bases.

In NPL 1, the difference in the blockage current derived from the kinds of base has been observed when the DNA has passed through the nanopore in the thin film. In NPL 1, to increase the identification rate of the blockage current, the nanopore is provided in a SiN membrane of the thin film, and the noise current is reduced by applying an insulating film and thus reducing the device capacity. In NPL 2, the nanopore is provided in a Graphene membrane of the thin film, and the noise current is reduced by using an insulating substrate and thus reducing the device capacity.

CITATION LIST

Non Patent Literature

NPL 1: Venta, K., et al., Differentiation of Short, Single-Stranded DNA Homopolymers in Solid-State Nanopores, ACS Nano 7(5), p. 4629-4636 (2013).
NPL 2: Kumar, A., et al., Noise and its reduction in grapheme based nanopore devices, Nanotech 24, 495503 (2013).

SUMMARY OF INVENTION

Technical Problem

A thin film for measuring a biopolymer has problems because the thin film is easily affected by the potential difference between the solutions at both sides of the thin film and may break due to the potential difference. In particular, when the device capacity is reduced to reduce the noise current, a problem arises because the thin film breaks easily.

It has been confirmed by an experiment that the noise current can be reduced by applying an insulating film to a device having a thin film membrane having a thickness of 12 to 20 nm and reducing the device capacity. At the same time, it has been newly found by our investigation this time that initial failure, namely the breakage of the thin film, is often caused when the chambers at both sides of the thin film of a noise-reduced low-capacity device are filled with solutions. NPL 1 and NPL 2 do not mention the initial failure, and the mechanism of the initial failure and the measures against the initial failure have been unknown.

As a result of investigation, the following findings have been made. When the solution tanks at both sides of the thin film are individually filled with solutions, an initial electric charge difference $\Delta Q$ is always caused between the solutions. Thus, the potential difference $\Delta V$ ($=\Delta Q/C$) applied to the thin film is amplified as the device capacity C decreases, and the initial failure is caused by the dielectric breakdown of the thin film.

Solution to Problem

The present application provides measurement procedures and mechanisms which do not cause the initial failure of the thin film when a biopolymer is analyzed using the thin film.

Because the initial failure of the thin film explained above is caused by the initial electric charge difference $\Delta Q$ between the solutions at both sides of the thin film, the initial failure can be avoided by conducting a procedure of removing the initial electric charge difference $\Delta Q$. In the conventional experimental procedures, both sides of the thin film have been filled individually with solutions which may cause an initial electric charge difference $\Delta Q$. Thus, the method provided by the application is characterized by having a structure for reducing the initial electric charge difference $\Delta Q$ between the solutions at both sides.

To solve the above problems, a typical biopolymer analysis apparatus of the invention has a thin film, a first solution in contact with a first surface of the thin film, a second solution in contact with a second surface of the thin film, potential difference adjustment means for adjusting the potential difference between the first solution and the second solution to a small value, a control unit for controlling the potential difference adjustment means, a biopolymer inlet from which a biopolymer is introduced to at least one of the first solution and the second solution, a first electrode provided in the first solution, a second electrode provided in the second solution and an ammeter for measuring the current which flows between the first electrode and the second electrode when the biopolymer passes through a hole in the thin film between the first solution and the second solution.

Moreover, a typical method for analyzing a biopolymer of the invention uses a thin film, a first solution in contact with a first surface of the thin film, a second solution in contact with a second surface of the thin film, a biopolymer inlet from which a biopolymer is introduced to at least one of the first solution and the second solution, a first electrode provided in the first solution, a second electrode provided in the second solution and an ammeter for measuring the current which flows between the first electrode and the second electrode when the biopolymer passes through a hole in the thin film between the first solution and the second solution. In the method, the potential difference between the first solution and the second solution is adjusted to a small value at least (1) until the first solution comes into contact with the first surface and the second solution comes into contact with the second surface, (2) until the first electrode is provided in the first solution and the second electrode is provided in the second solution or (3) while a third solution or the biopolymer is introduced.

Advantageous Effects of Invention

According to the invention, in an analysis apparatus having a thin film, the probability of the breakage of the thin film itself due to the potential difference caused between the solutions at both sides of the thin film by the introduction of the solutions and the like can be decreased considerably.

Problems, structures and effects other than those described above are explained by the description of embodiments below.

BRIEF DESCRIPTION OF DRAWINGS

FIG. 1A and FIG. 1B Sectional views of the thin film devices of Example 1

FIG. 2 A graph showing the relation between the device capacity and the noise current in Example 1

FIG. 3 A graph showing the relation between the noise current and the leak current in Example 1

FIGS. 4A, 4B and 4C The mechanisms for causing and avoiding the initial failure in Example 1

FIGS. 5A, 5B, 5C, 5D and 5E Measurement procedures of Example 1 in which a flow path is used as the potential adjustment means FIGS. 6A, 6B, 6C, 6D and 6E Measurement procedures of Example 1 in which a flow path is used as the potential adjustment means FIG. 7 A measurement procedure of Example 1 in which a flow path is used as the potential adjustment means FIG. 8 A measurement procedure of Example 1 in which a flow path is used as the potential adjustment means FIGS. 9A and 9B Measurement procedures of Example 1 in which a flow path is used as the potential adjustment means FIGS. 10A, 10B, 10C and 10D Measurement procedures of Example 2 in which a flow path is used as the potential adjustment means and the thin film devices are arrayed FIGS. 11A, 11B and 11C Measurement procedures of Example 2 in which a flow path is used as the potential adjustment means and the thin film devices are arrayed FIGS. 12A, 12B, 12C and 12D Measurement procedures of Example 3 in which a conductive wire is used as the potential adjustment means FIGS. 13A, 13B and 13C Measurement procedures of Example 3 in which a conductive wire is used as the potential adjustment means FIG. 14 A measurement procedure of Example 3 in which a conductive wire is used as the potential adjustment means FIG. 15 A measurement procedure of Example 3 in which a conductive wire is used as the potential adjustment means FIGS. 16A and 16B Measurement procedures of Example 3 in which a conductive wire is used as the potential adjustment means FIGS. 17A, 17B, 17C and 17D Measurement procedures of Example 4 in which a conductive wire is used as the potential adjustment means and the thin film devices are arrayed FIG. 18 A measurement procedure of Example 4 in which conductive wires are used as the potential adjustment means and the thin film devices are arrayed FIG. 19 A measurement procedure of Example 4 in which a conductive wire is used as the potential adjustment means and the thin film devices are arrayed FIG. 20 A measurement procedure of Example 4 in which conductive wires are used as the potential adjustment means and the thin film devices are arrayed FIGS. 21A, 21B, 21C and 21D Measurement procedures of Example 4 in which conductive wires are used as the potential adjustment means and the thin film devices are arrayed FIG. 22 A measurement procedure of Example 4 in which a flow path is used as the potential adjustment means and the thin film devices are arrayed

DESCRIPTION OF EMBODIMENTS

Embodiments of the invention are explained below according to the drawings.

Example 1

First, the effect of reducing the noise current following the reduction in the device capacity, the principle of occurrence of the initial failure associated with the reduction in the device capacity and the mechanism for preventing the initial failure are explained.

FIG. 1(A) is a sectional view of the produced thin film device. An insulating thin film 100 is supported on a conductive support 52, and both sides of the thin film 100 are filled with solutions 103 and 104. Here, the combined capacity C of the thin film device can be represented by $C=C_1+C_2$, where $C_2$ is the capacity of the part including the support 52, and $C_1$ is the capacity of the part which does not include the support 52 and in which the thin film 100 has a floating structure as in FIG. 1(A). Next, FIG. 1(B) is explained. FIG. 1(B) is a sectional view of a thin film device in which an insulating film 51 has been applied to the thin film 100 and the support 52. Also in this thin film device, the combined capacity C' can be calculated by $C'=C_1+C_2'$, where $C_2'$ is the capacity of the part including the support 52, and $C_1$ is the capacity of the part which does not include the support 52 and in which the thin film 100 has a floating structure. Here, $C_2>C_2'$ because the insulating film 51 has been applied in FIG. 1(B). The combined capacities also satisfy $C>C'$, and the device capacity decreases. Therefore, first, it was confirmed that when the amount of the applied insulating film 51 is increased, the noise current can be reduced by the reduction in the device capacity. As a result, as in NPL 1 and NPL 2, the noise current of the thin film device which we produced also decreased monotonously as the device capacity decreased (FIG. 2).

While it could be confirmed that the noise is reduced by applying an insulating film as described above, it has been found that the initial failure is caused as the device capacity decreases. The relation between the noise current (waveband of 1 MHz) and the initial leak current (applied voltage of 0.1 V) is shown in FIG. 3. When the initial failure was caused and the thin film 100 was broken, the device had a leak current even when low voltage of 0.1 V or the like was applied. The current value of a thin film device whose capacity was not reduced was $10^{-11}$ A or less, and the thin film 100 was not broken. However, the thin film 100 of a thin film device with a reduced capacity and a reduced noise current was broken, and a leak current of $10^{-11}$ A or more was caused.

The cause of the initial failure and the measures against the initial failure are explained using FIG. 4. When the solution tanks at both sides of the thin film 100 are individually filled with solutions, an initial electric charge difference ΔQ is always caused between the solutions. Thus, the potential difference ΔV (=ΔQ/C) applied to the thin film 100 is amplified as the device capacity C decreases, and the initial failure is caused by the dielectric breakdown of the thin film 100. The following explains the states when both sides of the thin film 100 are filled with solutions in such a manner that an initial electric charge difference ΔQ is caused in each of a normal thin film device whose capacity has not been reduced and a thin film device with a reduced capacity.

In FIG. 4(A), both sides of the thin film 100 of a normal thin film device whose capacity has not been reduced have been individually filled with first and second solutions 103 and 104 (FIG. 4(A-1 and A-2)). Here, when there is an initial electric charge difference ΔQ, for example when the first solution 103 contains many positively charged ions and charges 1 and the second solution 104 contains many negatively charged ions and charges 2, a potential difference ΔV (=ΔQ/C) is applied to the thin film 100 (FIG. 4(A-3)). However, the potential difference ΔV becomes small because the capacity C is large here, and the thin film 100 does not break when the potential difference ΔV does not exceed the dielectric breakdown voltage of the thin film 100. In FIG. 4(B), both sides of the thin film 100 of the thin film device with a reduced capacity have been individually filled with the first and second solutions 103 and 104 (FIG. 4(B-1 and B-2)). Here, as in FIG. 4(A), when there is an initial electric charge difference ΔQ, for example when the first solution 103 contains many positively charged ions and charges 1 and the second solution 104 contains many negatively charged ions and charges 2, a potential difference ΔV (=ΔQ/C') is applied to the thin film 100 (FIG. 4(B-3)). The potential difference ΔV becomes large because the capacity C' is small here, and the thin film 100 breaks when the potential difference ΔV exceeds the dielectric breakdown voltage of the thin film 100 (FIG. 4(B-4)).

The invention is characterized by adjusting the potential difference between both sides of the thin film 100 so that the initial electric charge difference ΔQ is not caused. That is, for example, when the solution is continuously supplied after filling one side of the thin film 100 with the first solution 103 as in FIG. 4(C-1) and both sides are filled with the same solution using a by-path flow path 105 or the like connecting the first and second solutions 103 and 104 at both sides of the thin film 100, the solutions can be supplied without causing an initial electric charge difference ΔQ (FIG. 4(C-2)). Here, the first and second solutions 103 and 104 are actually the same solution but are distinguished from each other here by the side of the thin film 100 (the front side or the back side) the solution is in contact with. In FIG. 4(C-3), the flow path 105 has been removed after supplying the first and second solutions 103 and 104. As a result, the initial failure, in which the thin film 100 is already broken when the first and second solutions 103 and 104 are supplied, can be prevented. This is the mechanism for removing the initial electric charge difference ΔQ used in the invention.

Next, the procedures used in the invention are explained in detail. In FIG. 5, a step of filling both sides of the thin film 100 with the first and second solutions 103 and 104 and connecting a first electrode 301 and a second electrode 302 in which the flow path 105 connecting the first solution 103 and the second solution 104 is used as the potential adjustment means is explained.

First, a step of fixing the thin film 100 in solution tanks 101 and 102 is explained. For the thin film device, for example, a device in which a SiN thin film 100 having a thickness of 20 nm and an area of 100 μm² or less is supported on a silicon support 52 having a thickness of 725 μm is used. Here, a device whose device capacity has been reduced for example by applying an insulating film to the thin film 100 or using $SiO_2$ for the support 52 may be used. Here, to sufficiently reduce the noise current as shown in FIG. 2, it is desirable to apply the insulating film in such a manner that the device capacity becomes 100 pF or less. Moreover, even in a device whose device capacity has not been reduced, the potential difference ΔV (=ΔQ/C) caused in the thin film 100 may exceed the dielectric breakdown voltage and the thin film 100 may be broken when the dielectric breakdown voltage of the thin film device is small or when the initial electric charge difference ΔQ caused between the upper and lower solutions is large. Thus, the procedure of the invention of adjusting the potential difference between both sides of the thin film 100 so as not to cause the initial electric charge difference ΔQ is effective also for a device whose device capacity has not been reduced.

For the thin film 100, a thin film having a hole having a diameter of 10 nm or less or the like for measuring the blockage current of DNA or the like may be used. The procedure of adjusting the potential difference between both sides of the thin film 100 is effective also for a thin film having a hole, because defects such as opening of a plurality of holes in the thin film 100 or an enlarged hole are caused when high voltage is applied to the thin film 100. Also, the material of the thin film 100 is not necessarily an inorganic material such as SiN or Graphene but may be an organic material such as a bionanopore in which a protein nanopore is embedded in a lipid bilayer.

The thin film 100 is fixed in the solution tanks 101 and 102 (FIG. 5(A)). An insulating material such as PMMA for example is used for the solution tanks 101 and 102, and the solution tanks 101 and 102 may have a flow path having a diameter of around 2 mm. The solution tanks 101 and 102 have inlets and outlets 201 to 204 for solutions. A member such as an O-ring for preventing a damage of the thin film or a liquid leakage may be inserted between the thin film 100 and the solution tanks 101 and 102. Small resistances of the solutions in the solution tanks lead to a reduction in the noise current. Thus, the length of the flow path in the solution tanks is desirably short and is for example 50 mm or less, and the flow path diameter is desirably large and is for example 1 mm or more. The structures in FIGS. 5 and 6 each have both solution tanks 101 and 102, but a structure having only one of the solution tanks 101 and 102 as in FIG. 7 may also be used to reduce the resistance of a solution.

Next, the flow path 105 connecting the first solution 103 and the second solution 104 is explained. The flow path 105 for connecting the first solution 103 and the second solution 104 is provided between the solution tank 101 and the solution tank 102. Although the inlet and outlet 202 and 203 are connected in FIG. 5 (B), a structure in which the inlet and outlet 201 and 204 or the like are connected may also be used. Alternatively, separate inlet and outlet may be provided in the solution tank 101 and the solution tank 102 to connect the flow path 105, and the inlet and the outlet may be connected. The flow path 105 may be an external pipe attached to the solution tank 101 and the solution tank 102 or the like or may have a structure which has been provided in the solution tank 101 and the solution tank 102 in advance. Because the dielectric breakdown of the thin film 100 can be prevented when the potential difference between the first solution 103 in the solution tank 101 and the second solution 104 in the solution tank 102 is small, the flow path diameter was 10 mm and the flow path length was 10 mm here so that the resistance of the solution in the flow path became small. Also, the flow path 105 desirably has a structure such as a valve 805 so that the first solution 103 and the second solution 104 can be separated and joined easily, according to the need, but an external flow path such as a pipe which can be removed as in FIG. 6 may also be used. The flow path 105 may have a structure having a plurality of inlets and outlets as in FIG. 8 so that the first solution 103 and the second solution 104 can be simultaneously supplied to the solution tank 101 and the solution tank 102. Moreover, opening and closing of the valve 805 may be able to be controlled by a computer 99 as a control device as in FIG. 5 that is programmed with instructions to open and close the valve.

Next, a step of bringing the first solution 103 and the second solution 104 into contact with the thin film 100 is explained. The solution tank 101 and the solution tank 102 are filled with the first solution 103 and the second solution 104 using an instrument such as a pipette 108. Ag/AgCl electrodes which have a simple structure and which can be handled easily were used here as an example of the first electrode 301 and the second electrode 302, and the first solution 103 and the second solution 104 here were an aqueous 1M KCl solution. The first solution 103 and the second solution 104 may contain DNA or the like which is a biopolymer to be measured. Although a step of supplying the solution from the inlet 201 is illustrated in FIG. 5(B), the solution may be supplied from 204 or the like. The solution supplied from the inlet 201 fills the solution tank 101, then passes through the flow path 105 and fills the solution tank 102 (FIG. 5(C)). As a result, the potential difference before the solutions come into contact with the thin film 100 can be made small as compared to the case in which the first solution 103 and the second solution 104 are individually supplied. Also, here, it is desirable to bring the second solution 104 into contact with the thin film 100 after waiting for one second or longer after once stopping the flow of the solution just before the second solution 104 comes into contact with the thin film 100 or by introducing the solution at a relatively slow flow rate of 10 µL/s or less. In this manner, the potential difference between the first solution 103 and the second solution 104 can be further reduced, and as a result the dielectric breakdown of the thin film 100 can be prevented.

When an air bubble is introduced when the solutions are supplied, the connection of the solutions is broken. Thus, the potential difference between the first solution 103 and the second solution 104 cannot be removed. Accordingly, it is desirable to take measures to use a flow path 105 having a structure with little unevenness and a polished surface or adjust the flow rate to 10 µL/s or less so that air is not introduced when the solutions are supplied.

The structure used for supplying the solutions may be a structure in which both sides of the thin film 100 are filled with the first solution 103 and the second solution 104 simultaneously using a flow path 705 which separates into two flows or more as in FIG. 8. Also, the solutions may be supplied using a structure in which the solutions are supplied after removing the potential difference between the solutions which fill both sides of the thin film 100 and in which the connection between the first solution 103 and the second solution 104 is already removed when the solutions are supplied as in FIG. 7. That is, because the original solutions are introduced from the same place, the potential difference between the solutions in contact with both sides of the thin film becomes small. Moreover, in the structure of FIG. 7, the solution tank is provided only at one side, and the solution is held by the surface tension of the first solution 103. Such a structure is advantageous because the measurement is possible even when the amount of the solution or the biopolymer is low. On the other hand, the structures of FIGS. 5 and 6 and the like, in which the solution tanks 101 and 102 are provided at both sides, are advantageous because the noise due to the vibration of the solutions during the measurement is not caused easily and because the measurement for a long time is possible since the evaporation of the solutions can be prevented due to the small interfaces between the solutions and the air.

While the first solution 103 and the second solution 104 are connected through the flow path 105 as in FIG. 5(C), operations of introducing a third solution for adding the amount of the first solution or the second solution or a third solution containing a biopolymer 110 to substitute a solution with the third solution, introducing the biopolymer 110 directly to the first solution or the second solution or taking out or putting in the first electrode 301 or the second electrode 302 may be conducted. This is because the potential difference between the solutions is removed through the flow path 105. Moreover, when an operation of leaving the device for one minute or longer with the solution tanks full with the first solution 103 and the second solution 104 or the like is conducted, a potential difference is sometimes caused due to the adhesion of a charged particle, the evaporation of the solutions or the like, and the thin film 100 is sometimes broken. Thus, it is desirable to similarly keep the connection between the first solution 103 and the second solution 104 through the flow path 105.

Then, in FIG. 5(D), the first electrode 301 and the second electrode 302 have been connected to the first solution 103 and the second solution 104, respectively. The first electrode 301 and the second electrode 302 here were Ag/AgCl electrodes as an example. Although the first electrode 301 and the second electrode 302 to be connected to a power supply 106 and an ammeter 107 have been connected to the first solution 103 and the second solution 104, respectively, while the first solution 103 and the second solution 104 are connected through the flow path 105 in FIG. 5(D), a procedure of providing the first electrode 301 and the second electrode 302 in the solution tanks 101 and 102 and then supplying the first solution 103 and the second solution 104 may also be used. The ammeter 107 may have a system in which the ammeter 107 is connected to a device such as the computer 99 and in which the measured current is stored as data, and the power supply 106 may also be connected to the computer 99 so that the applied voltage can be controlled.

Then, the connection between the first solution 103 and the second solution 104 has been broken in FIG. 5(E). Although the connection between the first solution 103 and the second solution 104 has been broken by closing the valve 805 included in the flow path 105 in FIG. 5 (E), a procedure of removing the flow path 105 or the like may also be used. Also, because the first electrode 301 and the second electrode 302 may have charges, the connection between the first solution 103 and the second solution 104 is desirably broken one second or longer after immersing the first electrode 301 and the second electrode 302 to be connected to the power supply 106 in the first solution 103 and the second solution 104. In this manner, the charges contained in the first electrode 301 and the second electrode 302 can be removed, and the potential difference between the first solution 103 and the second solution 104 after the connection is broken can be further reduced. As a result, the dielectric breakdown of the thin film 100 can be prevented.

In a configuration procedure which may also be used, the valve 805 of the flow path 105 is kept open while the third solution or biopolymer 110 is introduced to one of the first solution 103 and the second solution 104 after the solution tanks 101 and 102 are filled with the first solution 103 and the second solution 104 by the above method in such a manner that the potential difference between both sides of the thin film 100 becomes small. For example, while the solution tanks are filled with both the first solution 103 and the second solution 104 as shown in FIG. 9(A), the first solution 103 and the second solution 104 can be connected using the flow path 105, and the third solution or biopolymer 110 can be introduced from the inlets and outlets 201 to 204 (FIG. 9(B)). Then, the connection between the first solution 103 and the second solution 104 can be broken using the valve 805 or the like. Here, the first electrode 301 and the second electrode 302 can be immersed in the first solution 103 and the second solution 104 while the first solution 103 and the second solution 104 are connected using the flow path 105. Alternatively, the first electrode 301 and the second electrode 302 may be already immersed in the first solution 103 and the second solution 104 before the third solution or biopolymer 110 is introduced. By the above procedures, the thin film 100 can be prevented from being broken by the potential difference caused between the first solution 103 and the second solution 104 by the introduction of or the substitution with the biopolymer to be measured or a solution.

After introducing the biopolymer 110, the current which flows between the electrode 301 and the electrode 302 when the biopolymer 110 passes through the hole in the thin film 100 is measured by the ammeter 107. Thus, the sequence of the biopolymer can be measured by the difference in the value of the current which flows due to the difference in the molecules constituting the biopolymer (for example, the four kinds of bases when the biopolymer is DNA). The valve 805 may be controlled by a computer 99 as a control device that is programmed with instructions to maintain the valve 805 in an open state and closed state. The computer 99 may be programmed with instructions to maintain the valve 805 in the open state during a time when the biopolymer is introduced from the biopolymer inlet and maintain the valve 805 in a closed state during a time when the current that flows when the biopolymer passes through the hole in the thin film is measured.

Example 2

Although the cases in which one thin film device is used are explained in Example 1, similar procedures can be used also when thin film devices are arrayed. The points which are especially different from those of Example 1 are explained below. Thus, some of the methods and procedures for reducing the potential difference between the first solution 103 and the second solution 104, some of the operations which may be conducted when the potential difference has been reduced, some of the constituent parts and the like are not explained below.

A step of connecting the first electrode 301 and the second electrode 302 using the flow path 105 in the case in which the thin film devices are arrayed is shown in FIG. 10. A structure in which a plurality of electrodes 1301 or 1302 are connected to each of the first solution 103 and the second solution 104 is also possible. However, FIG. 10 is characterized by connecting a plurality of electrodes 1302 only to one side of the thin films 1100 and is advantageous because the number of electrodes is small and the circuit structure can be simplified.

In FIG. 10(A), the flow path 105 for connecting the first solution 103 and the second solution 104 is provided between the solution tank 101 and the solution tank 102. Although the inlet and outlet 202 and 203 are connected in FIG. 10(A), a structure in which the inlet and outlet 201 and 204 or the like are connected may also be used. Alternatively, separate inlet and outlet may be provided in the solution tank 101 and the solution tank 102 to connect the flow path 105, and the inlet and the outlet may be connected. The flow path 105 may be an external pipe attached to the solution tank 101 and the solution tank 102 or the like or may have a structure which has been provided in the solution tank 101 and the solution tank 102 in advance.

The solution tank 101 and the solution tank 102 are filled with the first solution 103 and the second solution 104 using an instrument such as the pipette 108. The first solution 103 and the second solution 104 may contain the biopolymer to be measured. Although a step of supplying the solution from the inlet 204 is illustrated in FIG. 10(B), the solution may be supplied from 201 or the like. The solution supplied from the inlet 204 fills the solution tank 102, then passes through the flow path 105 and fills the solution tank 101 (FIG. 10(C)). Moreover, while the first solution 103 and the second solution 104 are connected through the flow path 105 as in FIG. 10(C), operations of introducing the third solution or biopolymer 110 or taking out or putting in the first electrode(s) 301 or 1301 or the second electrode(s) 302 or 1302 or the like may be conducted. Moreover, when an operation of leaving the device for one minute or longer with the solution tanks full with the first solution 103 and the second solution 104 or the like is conducted, a potential difference is sometimes caused due to the adhesion of a charged particle, the evaporation of the solutions or the like. Thus, it is desirable to similarly keep the connection between the first solution 103 and the second solution 104 through the flow path 105.

Although a step of providing the first electrode 301 and the second electrodes 1302 in the solution tanks 101 and 102 before supplying the first solution 103 and the second solution 104 is supposed in FIG. 10, a structure in which the first electrode 301 and the second electrodes 1302 are provided in the solution tanks 101 and 102 after supplying the first solution 103 and the second solution 104 may also be used.

After supplying the first solution 103 and the second solution 104, the solutions in contact with the respective thin films 1100 are separated so that the arrayed electrodes of the first electrodes 1301 or the second electrodes 1302 composed of a plurality of electrodes are not electrically connected. As an example of the method for separating the solutions, in FIG. 10(D), the second electrodes 1302 have been provided on a member 1402 for isolating the solutions from each other, and the member 1402 has been closely adhered to the thin films 1100. Here, the member 1402 was for example an insulating rubber material for electrically separating the thin films 1100 and had a structure in which the electrodes 1302 stuck out of the rubber member 1402. When the member 1402 is closely adhered to the thin films 1100, the member 1402 is made closer at a speed of 10 mm/s or less or the like so as not to break the thin films 1100 with the water pressure caused by the close adhesion. Also, a control device such as the computer 99 may be used so that the speed for making the member 1402 closer can be controlled.

The connection between the first solution 103 and the second solution 104 through the flow path 105 is broken before or after closely adhering the member 1402 to the thin films 1100. However, it is desirable to break the connection after closely adhering the member 1402 to the thin films 1100 because the first solution 103 and the second solution 104 can be maintained at the same potential until the contact and the possibility of the dielectric breakdown of the thin films 1100 can be reduced.

An example of the method in which the member 1402 for separating the solutions filling the thin films 1100 does not have to be used is the constructing method of FIG. 11. The configuration procedures as in FIG. 11 may have a structure in which the solution tank is provided only at one side (FIG. 11(A)). After structuring the electrodes 302 and 1301, a flow path 905 and an instrument 908 for dropping a solution (FIG. 11(B)), the second solution 104 is supplied from the inlet 203 or the like, passes through the flow path 905 and the instrument 908 for dropping a solution and is dropped onto the upper parts of the thin films 1100 as first solutions 1103 (FIG. 11(C)). The third solution or biopolymer 110 can be easily introduced later to the first solutions 1103 when such a method is used. Thus, the method is advantageous because different samples of biopolymers can be supplied to the respective thin films 1100 and measured. In a constituent method other than that of FIG. 10, a structure which is different from that in FIG. 11 and in which the arrayed thin films 1100 each individually have the first solution 1103 and a second solution 1104 is also possible, and this structure can be achieved by a method in which the flow paths of the first solutions 1103 and the second solutions 1104 are individually connected or the like.

As in Example 1, in a configuration procedure which may also be used, the flow path 105 is used while the third solution or biopolymer 110 is introduced to one of the first solution 103 and the second solution 104 with the solution tanks 101 and 102 filled with the first solution 103 and the second solution 104. For example, while the solution tanks are filled with both the first solution 103 and the second solution 104, the first solution 103 and the second solution 104 can be connected using the flow path 105, and the third solution or biopolymer 110 can be introduced from the inlets and outlets 201 to 204. Then, the connection between the first solution 103 and the second solution 104 can be broken. Here, the first electrode 301 and the second electrode 302 can be immersed in the first solution 103 and the second solution 104 while the first solution 103 and the second solution 104 are connected using the flow path 105. Alternatively, the first electrode 301 and the second electrode 302 may be already immersed in the first solution 103 and the second solution 104 before the third solution or biopolymer 110 is introduced. By the above procedures, the thin film 100 can be prevented from being broken by the potential difference caused between the first solution 103 and the second solution 104 by the introduction of and the substitution with the biopolymer to be measured or a solution.

Example 3

Although the cases in which a flow path connecting the first solution and the second solution is used as the potential adjustment means are explained in Example 1, similar procedures can be used also when a conductive wire connecting the first solution and the second solution is used as the potential adjustment means. The points which are especially different from those of Example 1 are explained below. Thus, some of the timings for reducing the potential difference between the first solution 103 and the second solution 104, some of the operations which may be conducted when the potential difference has been reduced, some of the constituent parts and the like are not explained below.

The step of fixing the thin film 100 in the solution tanks is structured as in FIG. 5. Next, in FIG. 12(A), the first electrode 301 and the second electrode 302 having a conductive wire 2105 have been provided between the solution tank 101 and the solution tank 102. As an example, a structure in which a switch 2505 was provided to the conductive wire 2105 so that connection and disconnection of the wire could be operated easily and in which the potential difference could be adjusted was used here. In another structure capable of adjusting the potential difference, the first solution 103 and the second solution 104 are short-circuited using the wire 2105 which does not have the switch 2505 as in FIG. 13 or the first solution 103 and the second solution 104 are each grounded, and the potential difference may be adjusted by taking out or putting in the electrodes 2301 and 2302 connected to the wire 2105. Here, a control device such as the computer 99 may be used so that turning on and off of the switch 2505 or taking out and putting in of the wire 2105 can be controlled. For example, the control device may be programmed with instructions to open the switch 2505 when the current caused when the biopolymer passes through the hole in the thin film is measured. Also, although the first electrode 301 and the second electrode 302 serve both as the electrodes for connecting the power supply 106 and the solutions and as the electrodes for connecting the conductive wire 2105 and the solutions in FIG. 12, electrodes 2301 and 2302 for the conductive wire 2105 may be newly provided as in FIG. 13. Although the inlet and outlet 202 and 203 are connected in FIG. 12(A), a structure in which the inlet and outlet 201 and 204 or the like are connected may also be used. Alternatively, separate inlet and outlet may be provided in the solution tank 101 and the solution tank 102 to connect the conductive wire 2105, and the inlet and the outlet may be connected. Because it is desirable that the potential difference between the first solution 103 in the solution tank 101 and the second solution 104 in the solution tank 102 becomes small earlier, the resistance of the circuit to which the conductive wire 2105 was connected here was 1 k□ or less. Also, Ag/AgCl electrodes were used as the electrodes as an example. Here, when the electrodes are deteriorated, it takes time to remove the potential difference between the electrodes, and the thin film 100 may be broken due to the caused potential difference. Thus, electrodes which are less deteriorated are desirable.

Next, a step of bringing the first solution 103 and the second solution 104 into contact with the thin film 100 is explained. The solution tank 101 and the solution tank 102 are filled with the first solution 103 and the second solution 104 using an instrument such as the pipette 108. The first solution 103 and the second solution 104 may contain DNA or the like which is a biopolymer to be measured.

The procedures shown in FIG. 12(B and C) are examples, but the first solution 103 has been first supplied from the inlet 202, and the first electrode 301 and the first solution 103 have been brought into contact with each other. Then, the second solution 104 has been supplied from the inlet 204 so that the second electrode 302 and the second solution 104 would come into contact with each other. Here, when the time constant of the circuit connecting the first solution 103 and the second solution 104 through the conductive wire 2105 is large, it takes time until the potential difference between the first solution 103 and the second solution 104 is removed. Thus, it is desirable to bring the second solution 104 into contact with the thin film 100 after waiting for one second or longer after once stopping the flow of the solution just before the second solution 104 comes into contact with the thin film 100 or by introducing the solution at a flow rate of 10 µL/s or less, so that the potential difference between the first solution 103 and the second solution 104 becomes small before the second solution 104 comes into contact with the thin film 100. Here, as long as care is taken to make the potential difference between the first solution 103 and the second solution 104 in contact with the thin film 100 small through the conductive wire 2105, the order of supplying the first solution 103 and the second solution 104, the inlets used for supplying the solutions among the inlets 201 to 204 and the like are not necessarily as in FIG. 12. The procedure as in FIG. 14 in which the first solution 103 and the second solution 104 are simultaneously brought into contact with the thin film 100 may also be used. Also, as in FIG. 15, the solutions may be supplied using a structure in which the solutions are supplied after removing the potential difference between the solutions that fill both sides of the thin film 100 using the conductive wire 2105 and in which the first solution 103 and the second solution 104 are not electrically connected anymore at the point where the solutions are supplied. Moreover, while the first solution 103 and the second solution 104 are connected through the conductive wire 2105 in this manner, an operation which may cause the potential difference between the first solution 103 and the second solution 104, such as the introduction of the third solution or biopolymer 110, may be conducted. Alternatively, while the first solution 103 and the second solution 104 are electrically connected using the electrodes 2301 and 2302 connecting the conductive wire 2105, an operation of taking out or putting in the first electrode 301 and the second electrode 302 or the like may be conducted. Moreover, when an operation of leaving the device for one minute or longer with the solution tanks full with the first solution 103 and the second solution 104 or the like is conducted, a potential difference is sometimes caused due to the adhesion of a charged particle, the evaporation of the solutions or the like. Thus, it is desirable to keep the connection between the first solution 103 and the second solution 104 through the conductive wire 2105.

Although the first electrode 301 and the second electrode 302 for connecting with the power supply 106 are connected to the first solution 103 and the second solution 104, respectively, while the first solution 103 and the second solution 104 are connected through the conductive wire 2105 in FIG. 13, a procedure in which the first electrode 301 and the second electrode 302 are provided in advance in the solution tanks 101 and 102 and the first solution 103 and the second solution 104 are supplied may also be used.

The connection between the first solution 103 and the second solution 104 has been broken in FIG. 12(D) or FIG. 13(C). Although the connection of the circuit between the first solution 103 and the second solution 104 has been broken by turning off the switch 2505 of the conductive wire 2105 in FIG. 12(D), a procedure of removing the conductive wire 2105 as in FIG. 13(C) or the like may also be used. Here, because the first electrode 301 and the second electrode 302 may have charges, the connection of the circuit of the conductive wire 2105 is desirably broken one second or longer after immersing the first electrode 301 and the second electrode 302 connected to the power supply 106 in the first solution 103 and the second solution 104.

In a configuration procedure which may also be used, the conductive wire 2105 is used while the third solution or biopolymer 110 is introduced to one of the first solution 103 and the second solution 104 with the solution tanks 101 and 102 filled with the first solution 103 and the second solution 104 using the above procedures. For example, as shown in FIG. 16, while the solution tanks are filled with both the first solution 103 and the second solution 104, the circuit between the first solution 103 and the second solution 104 can be connected using the conductive wire 2105 (FIG. 16(A)), and the third solution or biopolymer 110 can be introduced from the inlets and outlets 201 to 204 (FIG. 16(B)). Then, the connection of the conductive wire 2105 can be broken. Here, the first electrode 301 and the second electrode 302 can be immersed in the first solution 103 and the second solution 104 while the circuit between the first solution 103 and the second solution 104 is connected using the conductive wire 2105 having the electrodes 2301 and 2302. Alternatively, the first electrode 301 and the second electrode 302 may be already immersed in the first solution 103 and the second solution 104 before the third solution or biopolymer 110 is introduced. By the above procedures, the thin film 100 can be prevented from being broken by the potential difference caused between the first solution 103 and the second solution 104 by the introduction of and the substitution with the biopolymer to be measured or a solution.

Example 4

Although the cases in which one thin film 100 is used are explained in Example 3, similar procedures can be used also when the thin film devices 1100 are arrayed, and a conductive wire connecting the first solution and the second solution can be used as the potential adjustment means. The method for arraying the thin film devices 1100 is similar to that of Example 2, and the method using the conductive wire can be conducted in a similar manner to that of Example 3. The points which are especially different from those of Examples 2 and 3 are explained below. Thus, some of the methods and procedures for reducing the potential difference between the first solution 103 and the second solution 104, some of the operations which may be conducted when the potential difference has been reduced, some of the constituent parts and the like are not explained below.

A part of an example of the step of supplying the first solution(s) 103 or 1103 and the second solution(s) 104 or 1104 using the conductive wire(s) 2105 or 3105 and connecting to the first electrode(s) 301 or 1301 and the second electrode(s) 302 or 1302 in the case in which the thin film devices are arrayed is shown in FIGS. 17 to 21.

FIGS. 17, 18 and 21 are characterized by connecting a plurality of electrodes 1301 or 1302 only to one side of the thin films 1100 and are advantageous because the number of electrodes is small and the circuit structure can be simplified. A structure in which a plurality of electrodes 1301 and 1302 are connected at both sides for both the first solution(s) 103 or 1103 and the second solution(s) 104 or 1104 as in FIG. 19 and FIG. 20 is also possible. FIG. 20 and FIG. 21 are advantageous because different samples of biopolymers can be supplied to the respective arrays and measured.

With respect to wiring, in FIG. 18 and the like, the arrayed electrodes 1302 in the second solution(s) 104 or 1104 each individually have the conductive wire 3105 and have a structure in which the electrode 1302 is connected to the electrode 301 or 1301 in the first solution 103 or 1103. Thus, also after completely adhering a rubber member 1401 or 1402 to the thin films 1100, the potential difference can be maintained small, and the potential difference is not further applied to the thin films 1100. Therefore, the possibility of the dielectric breakdown of the thin films 1100 can be further reduced.

On the other hand, in the structures of FIGS. 17 and 19, an electrode 3302 in the second solution 104 has one conductive wire 2105 and is connected to an electrode 3301 in the first solution 103. The structures are advantageous because there is only one conductive wire and thus the circuit does not become complicated.

When the solutions are supplied, the solution tank 101 and the solution tank 102 are filled with the first solution 103 and the second solution 104 using an instrument such as the pipette 108. The first solution(s) 103 or 1103 and the second solution (s) 104 or 1104 may contain a biopolymer to be measured.

With respect to the procedures of supplying the solutions, care should be taken to make the potential difference between the first solution(s) 103 or 1103 and the second solution(s) 104 or 1104 in contact with the thin films 1100 small through the conductive wire(s) 2105 or 3105 as in the cases shown in Example 3, and the procedures shown in FIG. 17 are examples thereof.

In FIG. 17(B), the second solution 104 has been first supplied from the inlet 203, and the electrode 3302 and the second solution 104 have been brought into contact with each other. Then, the first solution 103 has been supplied from the inlet 202 so that the electrode 3301 and the first solution 103 would come into contact with each other (FIG. 17(C)). Here, as long as care is taken to make the potential difference between the first solution 103 and the second solution 104 in contact with the thin films 1100 small through the conductive wire 2105, the order of supplying the first solution 103 and the second solution 104, the inlets used for supplying the solutions among the inlets 201 to 204 and the like are not necessarily as in FIG. 17. Moreover, while the first solution 103 and the second solution 104 are connected through the conductive wire 2105 in this manner, an operation of introducing the third solution or biopolymer 110 or the like may be conducted. Although a step of providing the first electrode 301, the second electrodes 1302 and the electrodes 3301 and 3302 in the solution tanks 101 and 102 before supplying the first solution 103 and the second solution 104 is supposed in FIG. 17, a procedure of providing the first electrode 301 and the second electrodes 1302 in the solution tanks 101 and 102 after supplying one of the first solution 103 and the second solution 104 may also be used. The configuration procedures and the operations are similar in FIGS. 18 to 21 and the like in which the arrayed electrodes 1301 and 1302 and the like are used.

In FIG. 17(D), after supplying the first solution 103 and the second solution 104, the solutions in contact with the respective thin films 1100 are separated so that the arrayed electrodes of the first electrodes 1301 or the second electrodes 1302 composed of a plurality of electrodes are not electrically connected. The method for separating the solutions is similar to the method of Example 2. When the member 1401 or 1402 is closely adhered to the thin films 1100, the member 1401 or 1402 is made closer at a speed of 10 mm/s or less or the like so as not to break the thin films 1100 with the water pressure caused by the close adhesion. The connection of the circuit between the first solution 103 and the second solution 104 by the conductive wire(s) 2105 or 3105 is broken before or after closely adhering the member 1401 or 1402 to the thin films 1100. However, it is desirable to break the connection after closely adhering the member 1401 or 1402 to the thin films 1100 because the first solution 103 and the second solution 104 can be maintained at the same potential until the contact and the possibility of the dielectric breakdown of the thin films 1100 can be reduced.

An example of the method in which the member 1402 for separating the solutions filling the thin films 1100 does not have to be used is the constructing method of FIG. 21. The configuration procedures as in FIG. 21 may have a structure in which the solution tank is provided only at one side. First, the solutions 1103 are dropped onto the upper surfaces of the thin films 1100 (FIG. 21(A)). Then, after structuring a structure in which the conductive wires 3105 connect both sides of the thin films 1100 using the electrodes 302 and 1301 (FIG. 21 (B)), the second solution 104 is supplied from the inlet 203 or the like so as to come into contact with the electrode 302 (FIG. 21 (C)), and at the end, the connection of the conductive wires 3105 is broken (FIG. 21 (D)). Use of such a method is advantageous because the measurement of different samples of biopolymers in the respective thin films 1100 is easy.

In a configuration procedure which may also be used, the conductive wire 2105 is used while the third solution or biopolymer 110 is introduced to one of the first solution 103 and the second solution 104 with the solution tanks 101 and 102 filled with the first solution 103 and the second solution 104. For example, while the solution tanks are filled with both the first solution 103 and the second solution 104, the circuit between the first solution 103 and the second solution 104 can be connected using the conductive wire 2105, and the third solution or biopolymer 110 can be introduced from the inlets and outlets 201 to 204. Then, the connection of the conductive wire 2105 can be broken. Here, the first electrode(s) 301 or 1301 and the second electrode(s) 302 or 1302 can be immersed in the first solution 103 and the second solution 104 while the circuit between the first solution 103 and the second solution 104 is connected using the conductive wire 2105 having the electrodes 3301 and 3302. Alternatively, the first electrode (s) 301 or 1301 and the second electrode (s) 302 or 1302 may be already immersed in the first solution 103 and the second solution 104 before the third solution or biopolymer 110 is introduced. By the above procedures, the thin film 100 can be prevented from being broken by the potential difference caused between the first solution 103 and the second solution 104 by the introduction of and the substitution with the biopolymer to be measured or a solution.

The configuration procedures described above can be modified to a structure in which a flow path is used as the potential adjustment means by substituting the conductive wire(s) 2105 or 3105 with the flow path 105 or the like and substituting the switch (switches) 2505 or 3505 with the valve 805 or the like. For example, when a flow path is used as the potential adjustment means in the structure of FIG. 18, the structure of FIG. 22 can be obtained.

The invention is not limited to the above Examples and includes variants of various kinds. For example, the Examples have been explained in detail to explain the invention simply and are not limited to those having all the explained components. A component of an Example can be replaced with a component of another Example, and a component of an Example can be added to a component of another Example. A component of each Example can be deleted or replaced with another component, or another component can be added. A part or the whole of the structures, the functions, the processing units, the processing means and the like may be achieved by hardware for example by designing with an integrated circuit. Moreover, the structures, the functions and the like may be achieved by software using a processor which reads and executes the programs for achieving the functions. The information on the programs, the tables, the files and the like for achieving the functions can be stored in a recording device such as a memory, a hard disk and an SSD (Solid State Drive) or in a recording medium such as an IC card, an SD card and a DVD.

INDUSTRIAL APPLICABILITY

The invention can be used for various analysis methods.

REFERENCE SIGNS LIST

1: positively charged ion or charge
2: negatively charged ion or charge
51: applied insulating film
52: thin film-supporting structure
99: control and measurement device (PC or the like)
100: thin film
101: solution tank
102: solution tank
103: solution
104: solution
105: flow path
106: power supply
107: ammeter
108: instrument for introducing solution (pipette or the like)
110: third solution or biopolymer
201: inlet and outlet
202: inlet and outlet
203: inlet and outlet
204: inlet and outlet
301: electrode
302: electrode
705: flow path separated into two flows or more
805: flow path-blocking means (valve or the like)
905: flow path
908: instrument connected to flow path for introducing solution (pipette or the like)
1052: arrayed thin films-supporting structure
1100: arrayed thin film
1103: first solution
1104: second solution
1106: arrayed power supply
1107: arrayed ammeter
1301: arrayed electrode
1302: arrayed electrode
1401: member for separating arrayed thin film devices
1402: member for separating arrayed thin film devices
2105: conductive wire
2505: switch
2301: electrode for conductive wire
2302: electrode for conductive wire
2908: instrument connected to electrode for introducing solution (pipette or the like)
3105: arrayed conductive wire
3301: electrode for conductive wire
3302: electrode for conductive wire
3505: arrayed switch

The invention claimed is:

1. A biopolymer analysis apparatus comprising:
a thin film,
a first solution associated with a first surface of the thin film,
a second solution associated with a second surface of the thin film,
a flow path having a valve, the valve connecting the first solution and the second solution,
a control unit that controls the flow path and an applied voltage across the thin film,
a biopolymer inlet from which a biopolymer is introduced to at least one of the first solution or the second solution,
a first electrode provided in the first solution,
a second electrode provided in the second solution, and
an ammeter connected to the first solution and the second solution, while the first solution and the second solution are connected through the flow path, that measures a current flowing between the first electrode and the second electrode when the biopolymer passes through a hole in the thin film between the first solution and the second solution,
wherein the control unit is programmed with instructions to maintain the valve in an open or a closed state,
wherein the control unit is programmed to:
during a time when the biopolymer is introduced from the biopolymer inlet, maintain the valve in the open state, and
during a time when the current that flows when the biopolymer passes through the hole in the thin film is measured, maintain the valve in the closed state.

2. The biopolymer analysis apparatus according to claim 1, wherein the control unit is programmed to, when the first solution comes into contact with the first surface and the second solution comes into contact with the second surface, keep the valve open.

3. The biopolymer analysis apparatus according to claim 2, wherein the control unit is programmed to, when the first electrode is provided in the first solution and the second electrode is provided in the second solution, maintain the valve open.

4. The biopolymer analysis apparatus according to claim 1, wherein the control unit is programmed to, when a third solution is introduced, maintain the valve open.

5. The biopolymer analysis apparatus according to claim 1, wherein the thin film has regions for measuring a plurality of biopolymers individually, the second electrode has a member having a plurality of electrodes corresponding to the regions, and the control unit is programmed with instructions to drive the member to hold the second solution in the regions and then closes the flow path.

6. The biopolymer analysis apparatus according to claim 1, further comprising:
a first tank comprising a first inlet and a first outlet, wherein the first inlet and the first outlet are on different sides of the first tank; and a second tank comprising a second inlet and a second outlet, wherein the second inlet and the second outlet are on different sides of the second tank;

wherein the flow path is positioned between the first and second tanks between the first inlet and the second outlet or between the second inlet and the first outlet; or wherein the first electrode is provided along the first inlet or the first outlet; and wherein the second electrode is provided along the second inlet or the second outlet.

7. A biopolymer analysis apparatus comprising:

a thin film;

a first solution associated with a first surface of the thin film;

a second solution associated with a second surface of the thin film;

a conductive wire connected to electrodes provided in the first solution and the second solution, wherein the conductive wire removes a potential difference between the first solution and the second solution through facilitating a continuous connection to the electrodes;

a control unit that controls the conductive wire and controls an applied voltage across the thin film;

a biopolymer inlet from which a biopolymer is introduced to at least one of the first solution or the second solution;

a first electrode provided in the first solution;

a second electrode provided in the second solution; and an ammeter that measures a current flowing between the first electrode and the second electrode when the biopolymer passes through a hole in the thin film between the first solution and the second solution, wherein the control unit is programmed with instructions to keep the conductive wire connected to the electrodes provided in the first solution and the second solution when at least one of a third solution and the biopolymer is introduced, and to keep the conductive wire unconnected during measurement of the current flowing between the first electrode and the second electrode when the biopolymer passes through the hole in the thin film.

8. The biopolymer analysis apparatus according to claim 7, wherein the conductive wire is a wire connecting the first electrode and the second electrode and has a change-over switch, and the control unit is programmed with instructions to open the change-over switch when the current caused when the biopolymer passes through the hole in the thin film is measured.

9. The biopolymer analysis apparatus according to claim 7, wherein the thin film has regions for measuring a plurality of biopolymers individually, the second electrode has a member having a plurality of electrodes corresponding to the regions, and the control unit is programmed with instructions to drive the member to hold the second solution in the regions and then disconnects the conductive wire.

* * * * *